United States Patent [19]

Jansen et al.

[11] Patent Number: 5,144,077
[45] Date of Patent: Sep. 1, 1992

[54] PROCESS FOR WORKING UP THE CRYSTALLIZATION MOTHER LIQUOR FROM THE RESOLUTION OF THE RACEMATE OF 1-(4-CHLOROPHENYL)-ETHYLAMINE

[75] Inventors: Johannes R. Jansen; Hans-Joachim Knops, both of Monheim, Fed. Rep. of Germany

[73] Assignee: Bayer Aktiengesellschaft, Leverkusen, Fed. Rep. of Germany

[21] Appl. No.: 798,678

[22] Filed: Nov. 26, 1991

[30] Foreign Application Priority Data

Dec. 11, 1990 [DE] Fed. Rep. of Germany ....... 4039447

[51] Int. Cl.$^5$ ................ C07C 209/84; C07C 209/86; C07C 209/88
[52] U.S. Cl. ................... 564/438; 564/302; 564/304
[58] Field of Search ........................ 564/438, 302, 304

[56] References Cited

U.S. PATENT DOCUMENTS 4,988,734  1/1991  Kraatz et al. ................. 514/624

FOREIGN PATENT DOCUMENTS 0341475  5/1988  European Pat. Off. .

Primary Examiner—Richard L. Raymond
Attorney, Agent, or Firm—Sprung Horn Kramer & Woods

[57] ABSTRACT

The invention relates to a process for working up to crystallization mother liquor which is obtained in the resolution of the racemate of 1-(4-chlorophenyl)-ethylamine of the formula (I) with S-(−)-N-phenylcarbamoyllactic acid of the formula (II) by removing the ethanol from the ethanolic crystallization mother liquor by distillation in a 1st step and stirring the residue which remains with tert.-butyl methyl ether or toluene in a second step and it being possible to employ the resulting crystalline salt of (R/S)-1-(4-chlorophenyl)-ethylamine and (S)-(−)-N-phenylcarbamoyllactic acid directly again for the resolution of the racemate. The (S)-form of the amine is mainly present in the mother liquor and can be racemised and added to the resolution of the racemate again.

4 Claims, No Drawings

PROCESS FOR WORKING UP THE CRYSTALLIZATION MOTHER LIQUOR FROM THE RESOLUTION OF THE RACEMATE OF 1-(4-CHLOROPHENYL)-ETHYLAMINE

The invention relates to a process for working up the crystallisation mother liquor which is obtained in the resolution of the racemate of 1-(4-chlorophenyl)-ethylamine of the formula (I) with S-(−)-N-phenylcarbamoyllactic acid of the formula (II).

This resolution of the racemate of 1-(4-chlorophenyl)-ethylamine, for example to give R-(+)-1-(4-chlorophenyl)-ethylamine, which can be used, inter alia, as an intermediate for the production of compounds having fungicidal activity, for example by reaction with S-(−)-N-phenyl-carbamoyllactic acid, is known (cf. U.S.P. 4,988,734). The ethanolic crystallisation mother liquor obtained in this process essentially contains S-(−)-1-4-chlorophenyl)-ethylamine and S-(−)-N- phenylcarbamoyllactic acid or its salt with racemic 1-4-chlorophenyl)-ethylamine. Until now, this crystallisation mother liquor and consequently expensive starting compounds was discarded, as no industrially practicable process was known for the isolation of these valuable compounds from the mother liquor.

The present invention relates to a process for working up the crystallisation mother liquor which is obtained in the resolution of the racemate of 1-4-chlorophenyl)-ethylamine of the formula (I) with S-(−)-N-phenyl-carbamoyllactic acid of the formula (II)

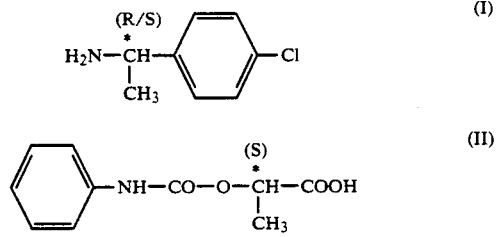

which is characterised in that, in a 1st step, the solvent ethanol, which is already present as a volatile component from the abovementioned resolution of the racemate in addition to the compounds already mentioned, is first removed from the crystallisation mother liquor by distillation under reduced pressure at a temperature between 0° C. and 60° C. and then in a second step the residue which remains is stirred at a temperature between 0° C. and 40° C. with tert.-butyl methyl ether or toluene and the resulting crystalline salt of racemic 1-4-chlorophenyl)-ethylamine and (S)-(−)-N-phenyl-carbamoyllactic acid of the following formula (III)

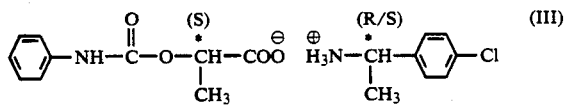

is isolated by filtering off with suction. The tert.-butyl methyl ether or toluene mother liquor contains almost quantitatively the 1-4-chlorophenyl)-ethylamine enriched in the (S)-enantiomer.

It is decidedly surprising to note that, with the aid of the process according to the invention, the valuable components of the crystallisation mother liquor from the resolution of the racemate described above can be recovered almost quantitatively in a simple manner.

This applies on the one hand to the (S)-(−)-phenylcarbamoyllactic acid, of which about 80% of the amount employed altogether for the resolution of the racemate of 1-4-chlorophenyl)-ethylamine (cf. EP-A 341,475) is used and is obtained as a salt with (R)-1-4-chlorophenyl)-ethylamine; the remaining approximately 20% of the amount employed is virtually quantitatively recovered in the process according to the invention, in fact surprisingly as a salt with racemic 1-4-chlorophenyl)-ethylamine. Precisely this salt can be employed again directly for the resolution of the racemate according to the known method (cf. EP-A 341,475). The isolation of the free (S)-(−)-N-phenylcarbamoyllactic acid from the salt with 1-4-chlorophenyl)-ethylamine is unnecessary. Thus the part of 1-4-chlorophenyl)-ethylamine which is present racemically as a salt with (S)-(−)-N-phenylcarbamoyllactic acid is recovered. The amine enriched in the (S)-enantiomer is present almost quantitatively in the tert.-butyl methyl ether mother liquor or the toluene mother liquor and can be reutilised again in a customary manner, for example by known racemisation processes and subsequent renewed resolution of the racemate.

A particular advantage of the process according to the invention is that in this case the use of water, which is otherwise frequently used as a solvent in working-up processes, can be entirely dispensed with. Expensive distillation steps and waste water problems are thus avoided. The organic solvents used in the process according to the invention, on the other hand, can be recovered by distillation with substantially less energy outlay than water and, if desired, introduced into the cycle again.

The following equation is again intended to give an overview of the process; the proportions indicated are only used for illustration, i.e. they are approximate values which, however, do not have to fully correspond to the preparatively indicated values:

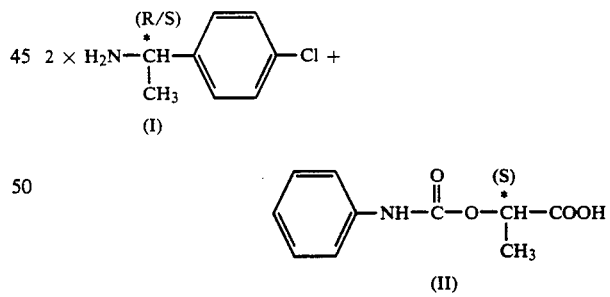

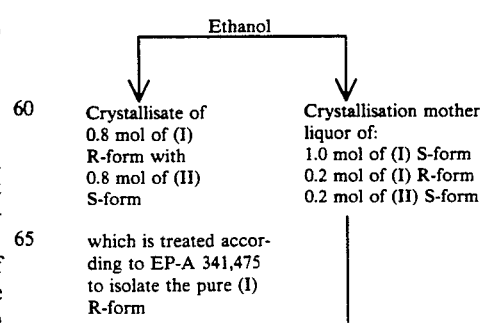

| | Ethanol | |
|---|---|---|
| Crystallisate of 0.8 mol of (I) R-form with 0.8 mol of (II) S-form | | Crystallisation mother liquor of: 1.0 mol of (I) S-form 0.2 mol of (I) R-form 0.2 mol of (II) S-form |
| which is treated according to EP-A 341,475 to isolate the pure (I) R-form | | |

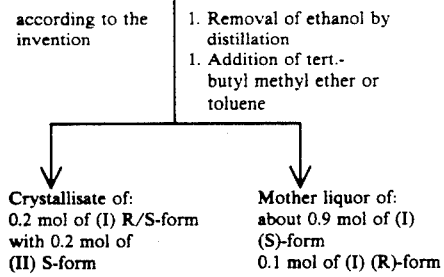

according to the invention
1. Removal of ethanol by distillation
1. Addition of tert.-butyl methyl ether or toluene Crystallisate of:
0.2 mol of (I) R/S-form
with 0.2 mol of
(II) S-form Mother liquor of:
about 0.9 mol of (I)
(S)-form
0.1 mol of (I) (R)-form The reaction conditions for the 1st step: the removal of the volatile components (ethanol) from the crystallisation mother liquor by distillation is in general carried out at temperatures between 0° C. and 60° C., preferably between 10° C. and 50° C., in particular between 20° C. and 40° C.

The removal of the volatile component from the crystallisation mother liquor by distillation is in general carried out under reduced pressure, preferably at pressures between 1 hPa and 100 hPa, in particular between 5 hPa and 50 hPa. The second step, stirring of the residue with tert.-butyl methyl ether or toluene, is in general carried out at temperatures between 0° C. and 60° C., preferably between 10° C. and 50° C., in particular between 15° C. and 45° C.

WORKING EXAMPLES

Example 1

The ethanol is removed by distillation in a water-jet vacuum at 20° C. to 40° C. from 600 ml of an ethanolic crystallisation mother liquor which is obtained in the resolution of the racemate of 1-4-chlorophenyl)-ethylamine of the formula (I) with S-(−)-N-phenylcarbamoyllactic acid of the formula (II) (as in EP-A 341,475), and which altogether contains 79 g (0.51 mol) of largely the (S)-form of 1-4-chlorophenyl)-ethylamine and 18 g (0.086 mol) of (S)-(−)-N-phenylcarbamoyllactic acid. The residue is stirred with 250 ml of tert.-butyl methyl ether at 15° C. to 25° C. for several hours, and the crystalline product is isolated by filtering off with suction and washed with 100 ml of tert.-butyl methyl ether. 30.6 g (98% of theory) of the salt of racemic 1-4-chlorophenyl)-ethylamine with (S)-(−)-N-phenylcarbamoyllactic acid are obtained.

The solvent is removed from the purified tert.-butyl methyl ether solutions by distillation in a water-jet vacuum. 60.4 g (about 0.38 mol) of crude 1-4-chlorophenyl)-ethylamine remain, the (R)-form to the (S)-form being present approximately in a ratio of 1:9 in this crude product.

Example 2

The ethanol is removed by distillation in a water-jet vacuum at 20° C. to 40° C. from 600 ml of an ethanolic crystallisation mother liquor which is obtained in the resolution of the racemate of 1-4-chlorophenyl)-ethylamine of the formula (I) with S-(−)-N-phenylcarbamoyllactic acid of the formula (II) (as in EP-A 341,475), and which altogether contains 79 g (0.51 mol) of largely the (S)-form of 1-4-chlorophenyl)-ethylamine and 18 g (0.086 mol) of (S)-(−)-N-phenylcarbamoyllactic acid. 265 ml of toluene are added to the residue at a temperature between 30° and 40° C. in the course of 30 minutes and the mixture is stirred at 40° C. for 12 hours. The crystalline product is then isolated by filtering off with suction (at 20° C.) and washed twice with 50 ml of toluene in each case. 31 g (99% of theory) of the salt of racemic 1-4-chlorophenyl)-ethylamine with (S)-(−)-N-phenylcarbamoyllactic acid are obtained.

We claim:

1. Process for working up the ethanolic crystallization mother liquor which is obtained in the resolution of the racemate of 1-(4-chlorophenyl)-ethylamine of the formula (I) with S-(−)-N-phenylcarbamoyllactic acid of the formula (II)

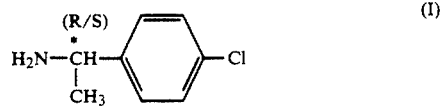

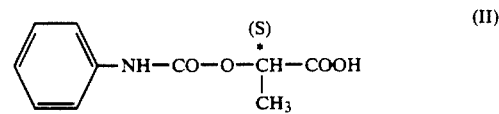

said crystallization mother liquor comprising ethanol, S-(−)-1-(4-chlorophenyl)-ethylamine, R-(+)-1-(4-chlorophenyl)-ethylamine and S-(−)-N-phenylcarbamoyl- acetic acid wherein, in a first step the solvent ethanol is removed by distillation and in a second step the residue is stirred with tert.-butyl methyl ether of toluene to form a crystalline salt of racemic 1-(4-chlorophenyl)-ethylamine and (S)-(−)-N-phenylcarbamoyllactic acid of the formula (III)

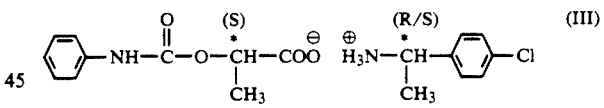

which is then isolated and the remaining mother liquor resulting after the present treatment comprises S-(−)-(4-chlorophenyl)-ethylamine and R-(+)-1-(4-chlorophenyl)-ethylamine.

2. Process according to claim 1, wherein the first step is carried out at a temperature between 0° C. and 60° C. and the second step is carried out at temperatures between 0° C. and 60° C.

3. Process according to claim 1, wherein the first step is carried out under reduced pressure.

4. Process according to claim 3, said pressure is between 1 hPa and 100 hPa.

* * * * *